United States Patent
Schrier et al.

(10) Patent No.: US 9,757,449 B2
(45) Date of Patent: Sep. 12, 2017

(54) ACCELERATION OF VECTOR VIRUS INDUCED IMMUNE RESPONSE IN AVIANS

(71) Applicant: Intervet Inc., Madison, NJ (US)

(72) Inventors: Carla Christina Schrier, Boxmeer (NL); Wilhelmus Gerardus Johannes Degen, Doetinchem (NL)

(73) Assignee: Intervet Inc., Madison, NJ (US)

(*) Notice: Subject to any disclaimer, the term of this patent is extended or adjusted under 35 U.S.C. 154(b) by 0 days.

(21) Appl. No.: 14/906,658

(22) PCT Filed: Jul. 25, 2014

(86) PCT No.: PCT/EP2014/066023
§ 371 (c)(1),
(2) Date: Jan. 21, 2016

(87) PCT Pub. No.: WO2015/011261
PCT Pub. Date: Jan. 29, 2015

(65) Prior Publication Data
US 2016/0158347 A1 Jun. 9, 2016

(30) Foreign Application Priority Data

Jul. 26, 2013 (EP) .................................. 13178137

(51) Int. Cl.
*A61K 39/39* (2006.01)
*A61K 39/12* (2006.01)
*A61K 39/17* (2006.01)
*C12N 7/00* (2006.01)
*C12N 15/117* (2010.01)
*A61K 39/00* (2006.01)

(52) U.S. Cl.
CPC ............... *A61K 39/39* (2013.01); *A61K 39/12* (2013.01); *A61K 39/17* (2013.01); *C12N 7/00* (2013.01); *C12N 15/117* (2013.01); *A61K 2039/5256* (2013.01); *A61K 2039/54* (2013.01); *A61K 2039/55561* (2013.01); *C12N 2310/17* (2013.01); *C12N 2710/16043* (2013.01); *C12N 2720/10034* (2013.01); *C12N 2760/18134* (2013.01)

(58) Field of Classification Search
None
See application file for complete search history.

(56) References Cited

U.S. PATENT DOCUMENTS

| | | | |
|---|---|---|---|
| 9,315,814 B2* | 4/2016 | Schrier | C12N 15/117 |
| 9,359,602 B2* | 6/2016 | Schrier | A61K 39/39 |
| 9,364,531 B2* | 6/2016 | Schrier | A61K 39/12 |
| 2003/0212028 A1* | 11/2003 | Raz | A61K 31/711 |
| | | | 514/44 R |
| 2014/0193457 A1* | 7/2014 | Schrier | C12N 15/117 |
| | | | 424/204.1 |
| 2014/0199345 A1* | 7/2014 | Schrier | A61K 39/39 |
| | | | 424/214.1 |
| 2014/0205633 A1* | 7/2014 | Schrier | A61K 39/12 |
| | | | 424/214.1 |

FOREIGN PATENT DOCUMENTS

| | | |
|---|---|---|
| EP | 2471926 A3 | 7/2012 |
| WO | WO8704663 A1 | 7/1987 |
| WO | WO 96/05291 * | 2/1996 |
| WO | WO 2006/079291 * | 8/2006 |
| WO | 2012089800 A1 | 7/2012 |
| WO | WO2012160183 A1 | 11/2012 |
| WO | WO2012160184 A1 | 11/2012 |
| WO | WO2013057235 A1 | 4/2013 |
| WO | WO2013057236 A1 | 4/2013 |
| WO | WO2013082327 A1 | 6/2013 |

OTHER PUBLICATIONS

Espacenet English translation of WO 2006/079291 of Aug. 2006 by Wang et al.*
Parvizi et al. (Vaccine. 2014; 32: 1932-1938).*
European Search Report for 13178137.9, mailed on Dec. 6, 2013, 7 pages.
International Search Report for PCT/EP2014/066023 mailed on Oct. 6, 2014, 13 pages.
Klinman D.M., CpG oligonucleotides accelerate and boost the immune system response elicited by AVA, the licensed anthrax vaccine, Expert review of vaccine, Future drugs, Jan. 1, 2006, 365-369, vol. 5., No. 1.
Klinman, D.M,, Immunotherapeutic uses of CpG oligodeoxynucleotides, The Journal of Immunology, Apr. 1, 2004, 249-258, vol. 4, No. 4, Nature Pub. Group.
Linghua, Z. et al, In vivo oral administration effects of various oligodeoxyneucleotides containing synthetic immunostimulatory motifs in the immune response to pseudorabies attenuated virus vaccine in newborn piglets, Vaccine, 2008, pp. 224-233, 26.
Rauw, F. et al., Improved vaccination against Newcastle disease by an in ovo recombinant HVT-ND combined with an adjuvanted live vaccine at day-old, Vaccine, Jan. 8, 2010, 823-833, vol. 28, No. 3.
Brownlie R. et al, Chicken TLR21 acts as a functional homologue to mammalian TLR9 in the recognition of CpG oligodeoxynucleotides, Molecular Immunology, Sep. 1, 2009, pp. 3163-3170, Vo.. 46, No. 15, WO.
Dar et al., Immunotherapeutic potential of CpG oligonucleotides in chickens, Japan Poultry Science Association, 2009, pp. 69-80, vol. 46.
Keestra, M et al., Chicken TLR21 is an innate CpG DNA receptor distinct from mammalian TLR9, The Journal of Immunology, Jul. 1, 2010, pp. 460-467, vol. 185, No. 1, WO.
Martinez-Martin, N. and Viejo-Borbolla, A., Toll-like receptor-mediated recognition of herpes simplex virus, Frontiers in Bioscience, 2010, pp. 718-729, S2.

* cited by examiner

*Primary Examiner* — Shanon A Foley

(57) ABSTRACT

The addition of an oligodeoxynucleotide that is an avian TLR21 agonist, to an avian Herpesvirus vector vaccine, provides an acceleration of the immune response against the antigen that is expressed and delivered by the Herpesvirus vector.

16 Claims, No Drawings

SEQUENCE LISTING

```
<160> NUMBER OF SEQ ID NOS: 17

<210> SEQ ID NO 1
<211> LENGTH: 30
<212> TYPE: DNA
<213> ORGANISM: Artificial Sequence
<220> FEATURE:
<223> OTHER INFORMATION: X4-I-minG

<400> SEQUENCE: 1 gggggtttc gttttttcgt ttttcgttt                               30

<210> SEQ ID NO 2
<211> LENGTH: 37
<212> TYPE: DNA
<213> ORGANISM: Artificial Sequence
<220> FEATURE:
<223> OTHER INFORMATION: X4-Li8

<400> SEQUENCE: 2
ggggggttcg tttttttcg tttttttcg ttggggg                        37

<210> SEQ ID NO 3
<211> LENGTH: 43
<212> TYPE: DNA
<213> ORGANISM: Artificial Sequence
<220> FEATURE:
<223> OTHER INFORMATION: X4-Bo9

<400> SEQUENCE: 3
```

```
gggggggtttt tttttcgttt tcgttttcgt tttttttttgg ggg              43

<210> SEQ ID NO 4
<211> LENGTH: 41
<212> TYPE: DNA
<213> ORGANISM: Artificial Sequence
<220> FEATURE:
<223> OTHER INFORMATION: X4-pent

<400> SEQUENCE: 4
ggggggttcg ttttcgtttt cgttttcgtt ttcgttgggg g                  41

<210> SEQ ID NO 5
<211> LENGTH: 47
<212> TYPE: DNA
<213> ORGANISM: Artificial Sequence
<220> FEATURE:
<223> OTHER INFORMATION: X4-III-trip

<400> SEQUENCE: 5 gggggggtttt tcgttttttt tttcgttttt ttttcgttt ttgggggg           47

<210> SEQ ID NO 6
<211> LENGTH: 46
<212> TYPE: DNA
<213> ORGANISM: Artificial Sequence
<220> FEATURE:
<223> OTHER INFORMATION: X4-IIq3-5

<400> SEQUENCE: 6
ggggggtttt cgtttttttt cgtttttttt cgtttttttt cgtttt            46

<210> SEQ ID NO 7
<211> LENGTH: 36
<212> TYPE: DNA
<213> ORGANISM: Artificial Sequence
<220> FEATURE:
<223> OTHER INFORMATION: X4-pent-3min5G

<400> SEQUENCE: 7
ggggggttcg ttttcgtttt cgttttcgtt ttcgtt                       36

<210> SEQ ID NO 8
<211> LENGTH: 36
<212> TYPE: DNA
<213> ORGANISM: Artificial Sequence
<220> FEATURE:
<223> OTHER INFORMATION: X4-II-minG

<400> SEQUENCE: 8
ggggggtttt cgtttttttt cgtttttttt cgtttt                       36

<210> SEQ ID NO 9
<211> LENGTH: 27
<212> TYPE: DNA
<213> ORGANISM: Artificial Sequence
<220> FEATURE:
<223> OTHER INFORMATION: X43-tri3g

<400> SEQUENCE: 9
ggggggttcg tcttcgtctt cgtcggg                                 27

<210> SEQ ID NO 10
<211> LENGTH: 35
<212> TYPE: DNA
<213> ORGANISM: Artificial Sequence
```

```
<220> FEATURE:
<223> OTHER INFORMATION: X43-quad

<400> SEQUENCE: 10 gggggggttcg tcttcgtctt cgtcttcgtc ggggg                              35

<210> SEQ ID NO 11
<211> LENGTH: 41
<212> TYPE: DNA
<213> ORGANISM: Artificial Sequence
<220> FEATURE:
<223> OTHER INFORMATION: X43-pent

<400> SEQUENCE: 11 gggggggttcg tcttcgtctt cgtcttcgtc ttcgtcgggg g                       41

<210> SEQ ID NO 12
<211> LENGTH: 39
<212> TYPE: DNA
<213> ORGANISM: Artificial Sequence
<220> FEATURE:
<223> OTHER INFORMATION: X43-II-5732

<400> SEQUENCE: 12 ggggggggttt tcgtctttt tcgtctttttt tcgtcttgg                          39

<210> SEQ ID NO 13
<211> LENGTH: 25
<212> TYPE: DNA
<213> ORGANISM: Artificial Sequence
<220> FEATURE:
<223> OTHER INFORMATION: X23N-6

<400> SEQUENCE: 13 ggggggggtcg tcgtcgtcgt cgtcg                                         25

<210> SEQ ID NO 14
<211> LENGTH: 35
<212> TYPE: DNA
<213> ORGANISM: Artificial Sequence
<220> FEATURE:
<223> OTHER INFORMATION: X23-quad

<400> SEQUENCE: 14 ggggggggtcg tcgtcgtcgt cgtcgtcgtc ggggg                              35

<210> SEQ ID NO 15
<211> LENGTH: 31
<212> TYPE: DNA
<213> ORGANISM: Artificial Sequence
<220> FEATURE:
<223> OTHER INFORMATION: X23n-8

<400> SEQUENCE: 15 ggggggggtcg tcgtcgtcgt cgtcgtcgtc g                                  31

<210> SEQ ID NO 16
<211> LENGTH: 43
<212> TYPE: DNA
<213> ORGANISM: Artificial Sequence
<220> FEATURE:
<223> OTHER INFORMATION: X23N-12

<400> SEQUENCE: 16 ggggggggtcg tcgtcgtcgt cgtcgtcgtc gtcgtcgtcg tcg                     43
```

```
<210> SEQ ID NO 17
<211> LENGTH: 41
<212> TYPE: DNA
<213> ORGANISM: Artificial Sequence
<220> FEATURE:
<223> OTHER INFORMATION: X23-pent

<400> SEQUENCE: 17 ggggggggtcg tcgtcgtcgt cgtcgtcgtc gtcgtcgggg g          41
```

ACCELERATION OF VECTOR VIRUS INDUCED IMMUNE RESPONSE IN AVIANS

CROSS-REFERENCE TO RELATED APPLICATIONS

This application is a national stage entry under 35 U.S.C. §371 of PCT/EP2014/066023, filed on Jul. 25, 2014, which claims priority to EP Application No. EP13178137.9, filed on Jul. 26, 2013. The content of PCT/EP2014/066023 is hereby incorporated by reference in its entirety.

The present invention relates to the field of veterinary vaccine immunology, and in particular to a vaccine comprising an avian Herpesvirus vector, an oligodeoxynucleotide, and a pharmaceutically acceptable carrier. Also the invention relates to methods for and uses of the vaccine and the oligodeoxynucleotide.

It has been well established that oligodeoxynucleotides can stimulate the innate immune system present in most vertebrates. This was first reported for the non-methylated CpG motifs present in bacterial DNA by Krieg et al. (1995, Nature, vol. 374, p. 546). In the subsequent two decades this process has been revealed as a part of the immediate response to the invasion of a micro-organism, by the recognition of conserved structures (so called pathogen-associated molecular patterns) existing e.g. in the genomic material of viruses and bacteria. For this purpose, the innate immune system employs specific pattern recognition receptors such as Toll-like receptors (TLRs).

TLRs are type I transmembrane glycoproteins, and the binding of an agonistic ligand induces the dimerization of TLRs which leads—for most TLRs—to the binding of MyD88. This initiates a cellular signalling cascade resulting in the activation of transcription factor NFkappaB. This in turn leads to the expression of type 1 interferons (IFN1$\alpha$ and IFN1$\beta$), and pro-inflammatory cytokines (interleukin (IL)1 beta, IL6, IL8, IL10, IL12, and tumour necrosis factor alpha). In addition this is a basis for the stimulation of the secondary, acquired immune response. (Kawai & Akira, 2010, Nature Immunol., vol. 11, p. 373).

In mammals the TLR dedicated to the detection of non-methylated CpG motifs is TLR9. However in the genome of avians, no TLR9 gene is present; instead a TLR21 was found to act as a functional homologue to mammalian TLR9 (Brownlie et al., 2009, Mol. Immunol., vol. 46, p. 3163; Keestra et al., 2010, J. of Immunol., vol. 185, p. 460). TLR21 has not been studied as extensively as TLR9, but the two share a number of functional similarities: specificity for non-methylated CpG motifs, and an intracellular localisation.

The use of an immunostimulatory non-methylated CpG-containing oligodeoxynucleotide (INO), as vaccine adjuvant has been described (Krieg, A. M., 2007, Proc. Am. Thorac. Soc., vol. 4, p. 289), also for veterinary applications. This was applied for example for poultry: in a vaccine to protect chickens against Newcastle Disease (Linghua et al., 2007, Vet. Immun. and Immunopath., vol. 115, p. 216); against infectious bursal disease (Mahmood et al., 2006, Vaccine vol. 24, p. 4838); or avian influenza (Hung et al., 2011, Vaccine, vol. 29, p. 29). For a review, see Dar et al. (2009, Japan Poultry Science, vol. 46, p. 69).

Recently several families of INOs have been disclosed, see: WO 2012/089.800 (X4 family), WO 2012/160.183 (X43 family), and WO 2012/160.184 (X23 family). These INOs are particularly effective as agonists for avian TLR21, causing a high immuno-modulatory effect at low concentrations. Their addition to a vaccine enhances the immunogenicity of the antigen component in that vaccine. Consequently, the amount of an antigen in a vaccine with such a TLR21 agonist could be reduced while achieving the same level of immunoprotection as without the agonist.

In mammals TLR9 is abundantly expressed on plasmacytoid dendritic cells. These cells are professional producers of type I interferons, which is a strong antiviral agent. Consequently an important activity of a TLR9 agonist is as antiviral agent, in particular against DNA viruses, such as Adenovirus or Herpesvirus; see Tang et al. (2010, Sci. China Life Sci., vol. 53, p. 172). This is very effective in practice, for example, Adenovirus that was to serve as vector for gene-delivery was rapidly cleared from an inoculated host by the antiviral effect of the TLR9 activation that was induced (Nayak & Herzog, 2010, Gene Ther., vol. 17, p. 295). Similarly, several types of Herpesviruses are effectively attacked by the innate immune system, such as HSV1, HSV2, VZV, and Cytomegalovirus (Yu et al., 2011, Cell. Mol. Immunol., vol. 8, p. 181; Gaajetaan et al., 2012, Antiviral Res., vol. 93, p. 39; Ong et al., May 2013, Blood, DOI 10.1182; Zhang et al., 2013, Plos One, vol. 8, e52003; and a review by Martinez-Martin, 2010, Frontiers in Biosc. S2, p. 718). This antiviral effect was also detected for a veterinary Herpesvirus: Pseudorabies virus infection in piglets (Linghua et al., 2008, Vaccine, vol. 26, p. 224).

In conclusion: TLR9 agonists are known to be strong immunostimulators, inducing the effective clearance of a viral infection, in particular of DNA viruses such as Herpesvirus.

A well-known way for the active vaccination of a target organism is by inoculation with a vector; typically this is a live recombinant micro-organism of low pathogenicity that replicates in the target, and expresses an antigen from a pathogenic micro-organism, against which the target is to be vaccinated. This is a convenient alternative to a classical inactivated vaccination which usually employs large amounts of antigen, in repeated doses, and an adjuvant to boost the target's immune system.

Characteristic for a vector vaccine, being a live and infectious micro-organism, is its ability to replicate. This replication provides a number of advantages, for example: the vector vaccine can be given in relatively low amounts, and the vector provides a long lasting presentation of the expressed antigen to the target's immune system.

In a way the inoculation of a target organism with a live recombinant vector vaccine is thus not much different from a 'normal' infection, and involves the establishment of a productive infection by the vector, and the induction of an immune response in the target. The development of immunity against the vector itself (if at all) may not be as relevant as that against the antigen that the vector delivers, by expression of a gene that is heterologous to the vector. This gene is typically derived from a micro-organism that is pathogenic to the target, and encodes a protein antigen (or the relevant part thereof) that induces a protective immunity against the pathogenic donor micro-organism.

Several types of vector vaccines are known, based on a diversity of micro-organisms such as viruses, bacteria, or parasites. A number of these are being used commercially, especially in the veterinary field, where the economy of a live vector vaccine is most relevant: a relatively cheap vaccine that can be administered to its targets by methods of mass vaccination. An outstanding example of a high volume, low margin veterinary market is poultry-breeding.

The most used viral vector vaccines for poultry are based on avian Herpesviruses such as duck enteritis virus (DEV), infectious laryngotracheitis virus (ILTV), or Herpes virus of turkeys (HVT).

DEV is an alphaherpesvirus that infects all ages of birds from the order Anseriformes (ducks, geese, and swans). It is also called Anatid Herpes Virus-1, or duck plague Herpesvirus. It has been used as vector vaccine against avian influenza (Liu et al., 2011, J. of Virol., vol. 85, p. 10989).

ILTV is also known as Gallid Herpesvirus 1, and causes severe respiratory infection in chickens and pheasants. In an attenuated form, it has also been used as vector against avian influenza (Pavlova et al., 2009, Vaccine, vol. 27, p. 773).

HVT is a virus from the family of Marek's disease viruses (MDV), which are alphaherpesviridae infecting avian species. HVT is a serotype 3 MDV, and is also known as: Meleagrid Herpesvirus 1, or turkey Herpesvirus. HVT was found to be completely apathogenic to chickens, and is a common vaccine, e.g. HVT strains FC-126, and PB1.

Serotype 2 MDV (MDV2, also known as Gallid Herpesvirus 3), is practically apathogenic to chickens. It has been used as a vector and as a vaccine, e.g. strain SB1. (Petherbridge et al., 2009, J. Virol. Meth., vol. 158, p. 11).

Serotype 1 MDV (MDV1, Gallid Herpesvirus 2) is originally pathogenic to poultry, but attenuated strains are known such as: RB1B, 814, and CVI-988 Rispens, which are used as vaccine or as live vector (Cui et al., 2013, PLoS One, 2013; 8(1): e53340)

MDV1, MDV2 and HVT are systemic viruses that can be applied as vaccines to chickens at an early age: at the day of their hatching from the egg (day one), or even before hatching, while still in the egg. This last approach, so-called 'in ovo vaccination', is a form of embryo vaccination, which is commonly applied around day 18 of embryonic development (ED), about 3 days before hatch.

HVT has been used as a live viral vector vaccine for a long time (see WO 87/04463), and for the expression and delivery of a variety of antigens from poultry pathogens, such as: the Newcastle disease virus (NDV) Fusion (F) protein (Sondermeijer et al., 1993, Vaccine, vol. 11, p. 349); the infectious bursal disease virus (IBDV) viral protein 2 (VP2) (Darteil et al., 1995, Virology, vol. 211, p. 481); the avian influenza virus (AIV) heamagglutinin (HA) protein (WO 2012/052.384); and the infectious laryngotracheitis virus (ILTV) gD and gI proteins (Hein et al., 2008, 43rd Natl. meeting Poultry Health & Processing, Ocean City, Md., p. 73-74). But also the expression has been described of a parasite antigen (Cronenberg et al., 1999, Acta Virol., vol. 43, p. 192). In a more recent development, HVT vector constructs have been described that express more than one heterologous gene, for example: the NDV F and the IBDV VP2 genes in WO 2013/057.235, and the NDV F and the ILTV gD/gI genes in WO 2013/057.236.

Consequently, a number of HVT vector vaccines for poultry are used commercially, for instance expressing the NDV F protein: Innovax™-ND (MSD Animal Health), and Vectormune™ HVT-NDV (Ceva); the IBDV VP2: Vaxxitek™ HVT+IBD (Merial; previously named: Gallivac™ HVT-IBD), and Vectormune™ HVT-IBD (Ceva); and the ILTV gD/gI: Innovax™-LT (MSD Animal Health).

One concern with the use of a live Herpesvirus as vector vaccine is the delay in the onset of immunity they require: because of its nature, a live vector, such as an (avian) Herpesvirus, first needs to establish a productive infection in the vaccinated target organism and replicate itself. Typically this will take about 3 to 7 days. Only then does any substantial level of expression of the heterologous gene occur, after which the target's immune system has to become activated against the expressed antigen; this takes 2-3 weeks. In total it may thus take up to 4 weeks to develop in a target an immune response that can effectively protect against a severe challenge by the pathogen that is the donor of the heterologous gene. This is not a major disadvantage when the target organism lives for years and has ample time to develop and strengthen its immunity. However in the case of poultry breeding the target's life span usually is short, and the field infection pressure is high.

Ways to increase the level of immunity in avians from vector vaccination, have been found in an increase of the expression level of the inserted heterologous gene, e.g. by optimising the strength of its promoter (see WO 2012/052.384). However, this has not lead to an earlier onset of immunity. Consequently there is a continued need in the field for an improvement of the immunisation of avians with live vector vaccines, in order to provide a protective immunity as early as possible.

Therefore it is an object of the present invention to overcome a disadvantage and solve a problem in the prior art, by providing for the early onset of immunity in avians against an antigen that is expressed and delivered by an avian Herpesvirus vector vaccine.

Surprisingly it was found that this object can be met by the use of an oligodeoxynucleotide that is an avian Toll-like receptor (TLR) 21 agonist. This provides an acceleration of the immune response in avians against an antigen expressed by an avian Herpesvirus vector vaccine.

For example it was found that where a protective immune response in young chickens against NDV from an HVT vector carrying the NDV-F gene normally takes 3-4 weeks post vaccination to develop, however, with the addition of an avian TLR21 agonist, an effective protection against a severe NDV challenge-infection was achieved already at two weeks p.v. When considered in relation to the 6 week life span of a broiler chicken, this 1-2 weeks earlier onset of immunity is a major acceleration of the vector's vaccination efficacy, and is of great relevance to the output of a commercial poultry operation.

This acceleration of vector-induced immunity could not be foreseen as the result of avian TLR21 activation, because this was known for its induction of a potent antiviral effect, similar to the activity of its functional homologue in mammals: TLR9. The inventors were therefore surprised to find that upon the addition of an avian TLR21 agonist, an avian Herpesvirus vector was not cleared rapidly, but on the contrary could proliferate and could express its heterologous gene. In particular, the avian herpesvirus vector could do this in a way that resulted in an immunity that was effective against the expressed antigen much earlier after vaccination, when compared to the immunisation without a TLR21 agonist.

It is currently not known how or why this phenomenon occurs, and because little is known of the workings of the avian (innate) immune system, no explanation is available from the prior art. Consequently it is not known if the observed effect of the TLR21 agonist is the result of an immune response that is faster, stronger, and/or more efficient in some way.

Without being bound to any theory or model that would explain these observations, the inventors speculate that the activation of the avian innate immune system by an avian TLR21 agonist, induces an immunological environment in the target avian that unexpectedly is supportive, rather than deleterious, for the replication of and the expression by an avian Herpesvirus vector.

Therefore in one aspect the invention relates to a vaccine comprising an avian Herpesvirus vector, an oligodeoxynucleotide, and a pharmaceutically acceptable carrier, wherein the avian Herpesvirus vector comprises a heterologous nucleotide sequence encoding an antigen from a micro-organism that is pathogenic to avians, and wherein the oligodeoxynucleotide is an avian Toll-like receptor (TLR) 21 agonist.

The vaccine according to the invention provides for an acceleration of the immune response in avians against a heterologous antigen expressed by an avian Herpesvirus vector.

A "vaccine" is well known to be a composition comprising an immunologically active compound, in a pharmaceutically acceptable carrier. The 'immunologically active compound', or 'antigen' is a molecule that is recognised by the immune system of the target and induces an immunological response. The response may originate from the innate or the acquired immune system, and may be of the cellular and/or the humoral type.

This immune response aids the vaccinated target animal in preventing, ameliorating, reducing sensitivity for, or treatment of a disease or disorder resulting from infection with a micro-organism. The protection is achieved as a result of delivering at least one antigen derived from that micro-organism. This will cause the target animal to show a reduction in the number, or the intensity, of clinical signs caused by the micro-organism. This may be the result of a reduced invasion, colonization, or infection rate by the micro-organism, leading to a reduction in the number or the severity of lesions and effects that are caused by the micro-organism, or by the target's response thereto.

The determination of the effectiveness of a vaccine according to the invention against an avian pathogen is well within the skills of the routine practitioner, for instance by monitoring the immunological response following vaccination, or after a challenge infection, e.g. by monitoring the targets' clinical signs of disease, clinical scoring, serological parameters, or by re-isolation of the pathogen, and comparing these results to responses seen in mock vaccinated animals.

Various embodiments and preferences of a vaccine according to the invention will be outlined below.

The term "comprising" (as well as variations such as "comprise", "comprises", and "comprised") as used herein, refer(s) to all elements, and in any possible combination conceivable for the invention, that are covered by or included in the text section, paragraph, claim, etc., in which this term is used, even if such elements or combinations are not explicitly recited; and does not refer to the exclusion of any of such element(s) or combinations. Consequently, any such text section, paragraph, claim, etc., can also relate to one or more embodiment(s) wherein the term "comprising" (or its variations) is replaced by terms such as "consist of", "consisting of", or "consist essentially of".

The term "avian" relates to an organism of the taxonomical class Aves; preferred avian organisms are avians of relevance to humans or to veterinary science, such as: chicken, turkey, duck, goose, partridge, peacock, quail, pigeon, pheasant, guinea fowl, finch, crow, parakeet, parrot, ara, macaw, cockatoo, finch, falcon, hawk, emu, cassowary, and ostrich. More preferred are avian organisms selected from the group consisting of: chicken, turkey, duck and goose. Most preferred is chicken. For the invention, an avian may be of any breed, type or variety, such as: layers, breeders, broilers, combination breeds, or parental lines of any of such breeds. Preferred types are: broiler, breeder, and layer. Most preferred are broiler chickens.

For the invention it is not necessary to have the same avian species as the target for vaccination, as the origin of the avian Herpesvirus vector, and as the origin of the micro-organism that is pathogenic to avians. One, two or all of these may be of different avian origin. For example: a vaccine for chickens, based a Herpesvirus vector from turkeys (HVT), expressing an HA antigen from avian influenzavirus isolated from a seagull.

A "Herpesvirus" is well known in the art, and is a virus belonging to the taxonomic family of the Herpesviridae. Preferred are Herpesviruses of the subfamily Alphaherpesvirinae. More preferred are DEV, ILTV, HVT, MDV2 and MDV1. Even more preferred are HVT, MDV2 and MDV1; most preferred is HVT.

Therefore, in a preferred embodiment of a vaccine according to the invention, the avian Herpesvirus vector is one or more selected from: duck enteritis virus, infectious laryngotracheitis virus, Herpesvirus of turkeys, Marek's disease virus serotype 2, and Marek's disease virus serotype 1.

A "vector" for the invention is well known in the art, as a live recombinant carrier micro-organism that survives in an inoculated avian target without apparent harm to the target, and expresses and delivers to the target's immune system an antigen expressed from a heterologous nucleotide sequence that it comprises. As will be apparent to a skilled person, a vector in principle can express and deliver more than one antigen, encoded by one or more heterologous gene(s).

Preferably the Herpesvirus vector for the vaccine according to the invention is derived from an established Herpesvirus vector vaccine, with a proven record of stable and effective replication and expression of the heterologous antigen.

For the construction of an avian Herpesvirus vector as described for the invention, the starting material is the Herpes virion, which is an enveloped virus particle, containing a relatively large genome of linear double stranded DNA. The avian Herpesviruses have a common and conserved genome organisation with unique long, and unique short regions, flanked by repeats. Several Herpesviral genomic sequences are publicly available, for example from GenBank™: DEV: EU082088, ILTV: NC_006623, HVT: AF291866, MDV2: HQ840738, and MDV1: AF147806.

Different molecular biological techniques can be used for the insertion of a heterologous nucleotide sequence into (avian) Herpesvirus vectors. For example for HVT, by using homologous recombination (Sondermeijer et al., 1993, supra), cosmid regeneration (U.S. Pat. No. 5,961,982), or Bacmids (bacterial artificial chromosomes) (Baigent et al., 2006, J. of Gen. Virol., vol. 87, p. 769). The preferred insertion techniques are by cosmid regeneration, e.g. as described in WO 93/25.665, or by using bacmids, as described in EP 996.738. This essentially employs a set of large overlapping sub-genomic fragments of the genome of the avian Herpesvirus vector to reconstruct a complete genome by cotransfection into host cells. As one of the cosmids carries an expression cassette, this becomes stably integrated into the genome of the avian Herpesvirus vector.

Also, several suitable, non-essential, locations for the insertion of a heterologous gene-construct into an avian Herpesvirus genome have been described; e.g. for HVT: in the unique short region (EP 431.668), or in the unique long genome region (WO 87/04463). Preferred insertion sites are the Us2 and Us10 sites.

In addition, different promoters have been described to drive the expression of a heterologous nucleotide sequence in avian Herpesvirus vectors, such as: the PRV gpX promoter (WO 87/04.463), the Rous sarcoma virus LTR promoter, the SV40 early gene promoter, the human cytomegalovirus immediate early1 (hCMV IE1) gene promoter (EP 719.864), and the chicken beta-actin gene promoter (EP 1.298.139).

The term "heterologous" for the invention, indicates that the nucleotide sequence is not present in the parental vector micro-organism that was used to generate the vector for the invention.

The term "nucleotide sequence" is known in the art as a molecular chain of nucleotides, with the capacity to 'encode' a protein antigen. This is a well-known concept in molecular biology and refers to the central dogma of molecular biology wherein a DNA sequence is transcribed into mRNA, and the mRNA is translated into the amino acid sequence of (a part of) a protein. This way a nucleotide sequence is "encoding" a protein.

To result in the actual expression of a protein antigen, the nucleotide sequence is preferably an open reading frame (ORF), indicating that it contains no undesired stop-codons that would prematurely terminate the transcription into mRNA. The nucleotide sequence may be a 'gene' (i.e. an ORF encoding a complete protein), or be a gene-fragment. It may be of natural or synthetic origin. Also, the nucleotide sequence needs to be under the control of a promoter sequence, which initiates the transcription process. This is commonly referred to as the promoter being "operatively linked" to the nucleotide sequence, where both are connected on the same DNA, in effective proximity, and with no signals or sequences between them that would intervene with an effective transcription.

For the invention, the promoter sequence used, can in principle be any promoter as long as an effective and sustained expression of the heterologous nucleotide sequence is provided.

The combination of nucleotide sequence and promoter is often termed an 'expression cassette'; such a cassette can conveniently be constructed, manipulated, and cloned using a carrier nucleic acid, such as a cloning plasmid. All this is well known in the art.

For the invention, the stable insertion of the heterologous nucleotide sequence into the genome of an avian Herpesvirus can be made by any suitable technique, provided the resulting recombinant Herpesvirus vector is able to display its favourable effects of safe, stable and effective expression of the heterologous antigen.

The nucleotide sequence for the invention preferably encodes a complete protein, but may also encode a section of a protein, for example the mature form of a protein, i.e. without a 'leader', 'anchor', or 'signal sequence'. The nucleotide sequence may even encode only a specific section of a protein, such as the section comprising an immunoprotective epitope.

In that regard a "protein" for the invention is a molecular chain of amino acids. The protein can be a native or a mature protein, a pre- or pro-protein, or an immunogenic fragment of a protein. Inter alia: peptides, oligopeptides and polypeptides are included within the definition of protein.

Typically the host cell in which the recombinant avian Herpesvirus vector replicates provides the bio-molecular machinery that drives the expression process. By modifying the relevant elements, the expression of an antigen can be optimised in e.g. timing, level, and quality; all this is within the routine capabilities of the skilled artisan.

An "oligodeoxynucleotide" is well known to mean a molecular chain of deoxynucleotides, a DNA that is relatively short, roughly between about 5 and about 500 nucleotides. Such a polymer molecule comprises deoxyriboses that are linked by phosphodiester bonds, and each carries an organic base: cytosine, thymine, adenine or guanine.

An oligodeoxynucleotide as described for the invention may comprise modifications, for example a modification of a phosphodiester bond to a phosphorothioate, a phosphorodithioate, or a dephospho bridge. Examples of dephospho bridges are methylhydroxylamine, formacetal and dimethylenesulfone groups.

Alternatively an oligodeoxynucleotide as described for the invention may comprise a modification concerning the replacement of a natural nucleoside base by a non-natural nucleoside base such as: 5-fluorocytosine, 7-deaza-7-substituted guanine, 7-deaza-8-substituted guanine, uracil, 2-thiouracil, dihydrouracil, 5-substituted uracil, 5-bromo-cytosine, 6-substituted adenine, 6-substituted cytosine, or N4-substituted cytosine.

Again other possible modifications concern the replacement of the deoxyribose sugar unit by a modified sugar unit, e.g. an L-2'-deoxyribose or 2'-L-arabinose.

Such modifications can be applied to modify or optimise the pharmacological characteristics of the oligodeoxynucleotide, such as its biological availability or half-life. For instance, the oligodeoxynucleotide can be formulated as a pharmaceutically acceptable salt, or be converted to a pharmaceutically acceptable ester or—ether, e.g. at the 5' or the 3' end hydroxyl group.

All these modification are well known to a skilled person, and can be applied using nothing but routine methods and materials.

In oligodeoxynucleotides used as mammalian TLR9 agonists, the use of phosphoro(di)thioate bonds was shown to be beneficial, improving both the stability as well as the immuno-stimulant activity. However for the present invention stability does not appear critical, and surprisingly it was found that in the interaction with avian TLR21, an oligodeoxynucleotide that was based entirely on phosphodiester bonds had a higher immuno-stimulant activity than a similar one, comprising phosphoro(di)thioate bonds.

Therefore, in a preferred embodiment the oligodeoxynucleotide for use in the invention as an avian TLR21 agonist, is in phosphodiester form.

A "pharmaceutically acceptable carrier" is an aid in the effective administration of the immuno-active compound of a vaccine, without causing (severe) adverse effects to the health of the target animal to which it is administered. Such a carrier can for instance be sterile water, physiological salt, or phosphate buffered saline solutions. In a more complex form the carrier can e.g. be a buffer, which can comprise further additives, such as stabilisers or preservatives. Details and examples are for instance described in well-known handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

For example, the standard stabiliser for HVT based live virus (vector) vaccines is: Nobilis™ Diluent CA, where CA stands for: cell associated; and which comprises in water for injection: sucrose, a pancreatic casein digest, a sodiumphosphate buffer, and a phenolphthaleine colorant. This HVT stabiliser can conveniently be used for the dilution, storage and administration of an avian TLR21 agonist as described for the invention. Other examples are:

An "antigen" for the invention is a protein (or an immunogenic part thereof) that can induce an immune response. Preferably the antigen is of a length, amino acid sequence, structure, form, or quality such that the immune response it induces in the vaccinated target is of sufficient strength to be protective against a pathogenic micro-organism.

A preferred antigen for use in the invention is a protein that is capable of inducing in a target a protective immunity against the micro-organisms from which that antigen was derived. Typically these are protein antigens that are expressed or presented on the outside of the micro-organism or its host cell; often such proteins are involved in processes that involve the infectivity, or virulence of the micro-organisms, such as proteins involved in interaction, attachment, and/or entry of host cells, invasion, nutrient uptake, motility, endo- or exo-toxicity, etc.

In case the micro-organism pathogenic to avians is a virus, such a protein antigen is for example: a viral envelope, capsid, or matrix protein, or a viral protein that allows the formation of virus like particles.

Preferred viral antigens for use in the invention are: NDV-F or -HN (haemagglutinin-neuraminidase), ILTV-gD and -gI, IBDV-VP2, IBV-S (spike) or -M (matrix), and AIV-HA, -NA, or -M (neuraminidase).

In the case of a bacterial micro-organism, a preferred protein antigen is a membrane protein such as an outer membrane protein, peptidoglycan, glycoprotein, lipoprotein, periplasmic membrane protein, or S-layer protein, or a protein from a pilus, porin, fimbriae or flagellum.

An antigen being "from a micro-organism" refers to the biological entity that is the origin of the nucleotide sequence encoding the antigen, and against which the Herpesvirus vector vaccine as described for the invention is intended to protect. The antigen-encoding nucleotide sequence can be derived from such micro-organism, either directly or indirectly. For example, by direct isolation from the micro-organism, or can be generated synthetically, using information from the micro-organism. The encoding nucleotide sequence obtained can be a DNA or an RNA molecule, depending on the source material used for its isolation. For expression by an avian Herpesvirus vector, the nucleotide sequence needs to be in DNA form. A skilled person is well aware of methods to isolate one or the other type of nucleic acid from a variety of starting materials, and of methods to convert one type into the other when needed.

Micro-organisms that are "pathogenic to avians" for the invention, are well known in the art. These include all types of micro-organisms: viruses, bacteria, parasites, fungi, rickettsia, protozoa, etc. A preferred micro-organism to serve as the origin of the nucleotide sequence encoding the one or more antigen(s) expressed by the Herpesvirus vector as described for the invention, is selected from: a virus, a bacterium, a parasite, and a fungus, all of which are pathogenic to avians.

In a preferred embodiment the virus pathogenic to avians is selected from: infectious bronchitis virus, NDV, avian Adenovirus, avian Astrovirus, avian paramyxovirus, Egg drop syndrome virus, fowl adenovirus, IBDV, chicken anaemia virus, avian encephalo-myelitis virus, fowl pox virus, turkey rhinotracheitis virus, duck plague virus, duck viral hepatitis virus, pigeon pox virus, MDV, avian leucosis virus, ILTV, avian metapneumovirus, avian influenza virus, goose parvovirus, and Reovirus.

In a preferred embodiment the bacterium pathogenic to avians is selected from the bacterial genera: *Escherichia*, *Salmonella*, *Ornithobacterium*, *Haemophilus*, *Pasteurella*, *Bordetella*, *Erysipelothrix*, *Mycoplasma*, *Campylobacter*, *Borrelia*, *Enterococcus*, *Avibacterium*, *Riemerella*, *Listeria*, *Shigella*, *Streptococcus*, *Staphylococcus*, *Mycobacterium*, *Chlamydia* and *Clostridium*.

In a preferred embodiment the parasite pathogenic to avians is selected from the parasite genera: *Eimeria* and *Cryptosporidium*.

In a preferred embodiment the fungus pathogenic to avians is selected from the fungal genera: *Aspergillus* and *Candida*.

In a preferred embodiment of the vaccine according to the invention, the avian Herpesvirus vector is HVT and the avian TLR21 agonist is X4-I-minG (SEQ ID NO: 1).

In a preferred embodiment of the vaccine according to the invention, the avian Herpesvirus vector is HVT and the avian TLR21 agonist is X4-pent (SEQ ID NO: 4).

These micro-organisms and their diseases are well known in the art, and are e.g. described in well-known handbooks, like: "The Merck veterinary manual" (10th ed., 2010, C. M. Kahn edt., ISBN: 091191093X), and: "Diseases of Poultry" (12th ed., 2008, Y. M. Saif edt., ISBN-10: 0813807182).

For the invention, the names of the micro-organisms used herein, such as of the Herpesvirus vector, and of the micro-organisms pathogenic to avians, are presented here as they are currently used in the scientific literature. Consequently these names refer to the micro-organisms that are currently classified within the taxonomic groups with those names. The invention includes also micro-organisms that are sub-classified therefrom in any way, for instance as a subspecies, strain, isolate, genotype, variant or subtype and the like. These micro-organisms share the characterising features of their taxonomic group-members such as in their morphologic, genomic, and biochemical characteristics, as well as their biological characteristics such as physiologic, immunologic, or parasitic behaviour. As is known in the field, the classification of micro-organisms is based on a combination of such features.

It will be apparent to a skilled person that while the micro-organisms that are the subject of the present invention are currently classified in these groups by e.g. genus or species, this is a taxonomic classification that could change as new insights lead to reclassification into a new or different taxonomic group. However, as this does not change the micro-organisms itself, or its antigen repertoire, but only its scientific name or classification, such re-classified micro-organisms remain within the scope of the invention.

An "avian Toll-like receptor 21" is well known in the art, and the DNA and amino acid sequences of several such receptors are available from public databases; either as a separate gene or protein, as part of a genomic sequence, or as a section of the gene, indicating differences to known TLR21 sequences. For example from GenBank: for chicken: NM_001030558 and NW_003763865. Other avian TLR21 sequences have also been disclosed, e.g. for finch, falcon and robin, respectively: GU904859, GU904941, and JX502652. Also the TLR21 of different chicken types and breeds were disclosed. For reference, see: Ciraci & Lamont, 2011, Dev. & Comp. Immunol., vol. 35, p. 392; Alcaide & Edwards, 2011, Mol. Biol. Evol., vol. 28, p. 1703; and: Ruan et al., 2012, Poultry Sci., vol. 91, p. 2512.

In addition, the inventors have found that further avian TLR21 sequences are publicly available, albeit unannotated or incorrectly annotated; for example the gene for a Turkey TLR21 is available under accession no. XM_003209691, where it is labelled as being "TLR13-like". See also Ramasamy et al. (2012, Mol. Biol. Rep., vol. 39, p. 8539). Nevertheless, this gene displayed significant homology to a chicken TLR21 gene, and when cloned into the HEK293 cell/pNifTy2 indicator system, this turkey TLR was highly responsive to non-methylated CpG motifs. The subcloned Turkey TLR21 was tested with a mammalian TLR9 agonist '2006' and with some of the avian TLR21 agonists described herein: '2006' was found to have an EC50 on this receptor of 6.6 nM, which was comparable to that for 'X4-I-minG', but 'X4-pent' was more active, and had an EC50 of 1.6 nM.

The HEK293 cell/pNifTy2 indicator system can be used to screen and qualify TLR21 agonists, as well as TLR21 receptors. It is based on detecting the activation of NFkappaB resulting from the activation of a receptor—here avian TLR21—that the cells display, through the detection of a marker gene expression by colour reaction. This is e.g. described in WO 2012/089.800, and allows convenient, fast, and side-by-side comparison of large numbers of candidate agonist molecules, in a range of concentrations. Other detector systems for avian TLR21 activation have also been described, for example using the HD11 chicken macrophage cell-line (Ciraci & Lamont, supra), excreting nitrogen monoxide upon CpG stimulation. Other cell-systems may employ transiently transfected cells, and in vivo tests are equally possible.

Consequently, a skilled person is well capable of identifying avian TLR21 gene- and protein-sequences, as well as confirming that the encoded protein is indeed a receptor for unmethylated CpG motifs.

In a similar way the detection whether an oligodeoxynucleotide is an avian TLR21 "agonist" for the invention can conveniently be done, e.g. using an established avian TLR21. An agonist is defined in the art as a compound that can bind to a biological receptor and trigger its activation or response. For the invention, an agonist for an avian TLR21 comprises an unmethylated CpG motif. Using a detector cell-system, or an in vivo model, such an agonist will stimulate a level of activity from the TLR21 that is above its resting, unactivated state. Preferably the agonist's activity is high to very high; this can be established using low to very low concentrations of the agonist. For example, where a well-known standard CpG oligodeoxynucleotide such as 'ODN 2006' (Krug et al., 2001, Eur. J. Immunol., vol. 31, p. 2154) will activate an avian TLR21 when in the micromolar or high nanomolar range; a preferred oligodeoxynucleotide for the invention is active in low nanomolar, or even in picomolar concentration range.

One convenient way to establish and compare the agonist activity of an avian TLR21 agonists for the invention, is by determining their EC50 value, for example in the HEK293 cell/pNifTy2 indicator system expressing an avian TLR21, as described in WO 2012/089.800. The EC50 value is the half-maximal effective concentration, and represents the concentration of oligodeoxynucleotide that is necessary to induce an amount of the reporter enzyme SEAP in the reporter cell system used, that gives a half-maximal absorption. Preferred TLR21 agonists for use in the invention have an EC50 value in the nanomolar, or even in the picomolar range.

Therefore, for the invention, a preferred avian TLR21 agonist has an EC50 value below 1 mM, more preferably below 500 nM, 100 nM, 10 nM, 1 nM, 500 pM, 100 pM, or even below 50 pM, in order of increasing preference.

Such highly active avian TLR21 agonists have been described in the prior art, for example the X4 (WO 2012/089.800), X43 (WO 2012/160.183), and X23 (WO 2012/160.184) families of compounds. These compounds are strong TLR21 agonists, activating an avian TLR21 even when in very low concentrations.

Therefore in a preferred embodiment of a vaccine according to the invention, the avian TLR21 agonist is selected from the X4, X43, or X23 family.

It goes without saying that the vaccine according to the invention can also comprise more than one TLR21 agonist, and these can be selected from one, two or from all three of these compound families.

The X4 family of TLR21 agonists is disclosed in WO 2012/089.800; its disclosure is hereby incorporated by reference in its entirety.

Therefore in a preferred embodiment of a vaccine according to the invention, the avian TLR21 agonist has the general formula: 5'-[N1]x [N7]r {N3 [N4]p C G [N5]q N6}n [N8]s [N2]z-3', wherein: N1=C or G; N2=C or G; N3=T, C or G; N4=C or T, provided when N3=C, then N4=T; N5=C or T; N6=A, T, G or C; N7=A, T, C or G; N8=A, T, C or G; x=3-10; n=2-100; z=0-10; r=0-8, provided when N7=T, then r=1-25; p=1-6, provided when N4=T, then p=1-25; q=1-6, provided when N5=T, then q=1-25; and s=0-8, provided when N8=T, then s=1-25.

The X43 family of TLR21 agonists is disclosed in WO 2012/160.183; its disclosure is hereby incorporated by reference in its entirety.

Therefore in a preferred embodiment of a vaccine according to the invention, the avian TLR21 agonist has the general formula: 5'-[G]x {[T]p T T C G T C [T]q}n [G]z-3', wherein: p=1-15; q=1-15; n=2-100; x=3-10; and z=0-10.

The X23 family of TLR21 agonists is disclosed in WO 2012/160.184; its disclosure is hereby incorporated by reference in its entirety.

Therefore in a preferred embodiment of a vaccine according to the invention, the avian TLR21 agonist has the general formula: 5'-[G]x {T C G T C G}n T C G [G]z-3', wherein: x=3-20; z=0-10; and n=2-100.

TLR21 agonists as described for the invention can be produced in different ways, all known in the art. (Ellington & Pollard, 2001, in: Synthesis and purification of oligonucleotides. Current Protocols in Molecular Biology, unit 2.11, p. 1-25; J. Wiley & sons Inc.). In addition, many commercial suppliers offer custom synthesis of an oligodeoxynucleotide, with modifications as desired, at any scale. For example: BioSpring (Frankfurt a. M., Germany), and Eurofins MWG Operon (Ebersberg, Germany).

While exploring the present invention, it was found that the TLR21 agonists as described for the invention in general have a stronger agonist activity when they are longer; especially oligonucleotides over 100 nucleotides in length are highly active. However such long oligodeoxynucleotides become increasingly difficult to synthesize reliably, and to purify. Also for veterinary applications, longer oligodeoxynucleotides rapidly become too expensive. Therefore a TLR21 agonist for use in a vaccine according to the invention is preferably between about 20 and about 70 nucleotides in length, more preferably between 22 and 60, between 25 and 50, between 30 and 45, or even between about 30 and about 40 nucleotides, in order of increasing preference.

Similarly it was found that the TLR21 agonist's as described for the invention are more active as avian TLR21 agonists when the stretch of G nucleotides to the 3' (i.e. downstream) end of the CpG motif is shorter, or even absent, and the stretch of G nucleotides to the 5' (i.e. upstream) end of the CpG motif is longer.

This was unexpected, and a difference between avian TLR21 and mammalian TLR9, as the inventors observed that for mammalian TLR9 agonists the activity is higher with a short/absent 5' G stretch, and a long 3' G stretch.

Therefore in a preferred embodiment of a TLR21 agonist from the X4 family: s=0, and z=0.

cally acceptable carrier for the invention, this result in the vaccine according to the invention.

TABLE 1

Further preferred avian TLR21 agonists for use in the invention

| Avian TLR 21 agonist | Nucleotide sequence | Length | EC50 | SEQ ID NO: |
|---|---|---|---|---|
| X4 family: | | | | |
| X4-I-minG | GGGGGGTTTCGTTTTTTCGTTTTTTCGTTT | 30 | 1.9 nM | 1 |
| X4-Li8 | GGGGGGTTCGTTTTTTTCGTTTTTTTCGTTGGGGG | 37 | 950 pM | 2 |
| X4-Bo9 | GGGGGGTTTTTTTTCGTTTCGTTTTCGTTTTTTTTGGGGG | 43 | 714 pM | 3 |
| X4-pent | GGGGGGTTCGTTTTCGTTTTCGTTTTCGTTTTCGTTGGGGG | 41 | 430 pM | 4 |
| X4-III-trip | GGGGGGTTTTCGTTTTTTTTTCGTTTTTTTTCGTTTTTGGGGG | 47 | 330 pM | 5 |
| X4-IIq3-5 | GGGGGGTTTTCGTTTTTTTCGTTTTTTTCGTTTTTTTCGTTTT | 46 | 70 pM | 6 |
| X4-pent-3min5G | GGGGGGTTCGTTTTCGTTTTCGTTTTCGTTTTCGTT | 36 | 25 pM | 7 |
| X4-II-minG | GGGGGGTTTTCGTTTTTTTCGTTTTTTTCGTTTT | 36 | 23 pM | 8 |
| X43 family | | | | |
| X43-tri3g | GGGGGGTTCGTCTTCGTCTTCGTCGGG | 27 | 700 pM | 9 |
| X43-quad | GGGGGGTTCGTCTTCGTCTTCGTCTTCGTCGGGGG | 35 | 560 pM | 10 |
| X43-pent | GGGGGGTTCGTCTTCGTCTTCGTCTTCGTCTTCGTCGGGGG | 41 | 400 pM | 11 |
| X43-II-5732 | GGGGGGGTTTTCGTCTTTTTCGTCTTTTTCGTCTTGG | 39 | 55 pM | 12 |
| X23 family | | | | |
| X23N-6 | GGGGGGGTCGTCGTCGTCGTCGTCG | 25 | 600 pM | 13 |
| X23-quad | GGGGGGGTCGTCGTCGTCGTCGTCGTCGGGGG | 35 | 390 pM | 14 |
| X23n-8 | GGGGGGGTCGTCGTCGTCGTCGTCGTCG | 31 | 250 pM | 15 |
| X23N-12 | GGGGGGGTCGTCGTCGTCGTCGTCGTCGTCGTCGTCG | 43 | 250 pM | 16 |
| X23-pent | GGGGGGGTCGTCGTCGTCGTCGTCGTCGTCGTCGGGGG | 41 | <200 pM | 17 |

In a preferred embodiment of a TLR21 agonist from the X43 family: z=0.

And, in a preferred embodiment of a TLR21 agonist from the X23 family: z=0.

Further preferred embodiments of a TLR21 agonist from the X4 family are where: N1=G; N7=G; r=3-8 (preferably r=5); N3=T; N4=T; p=2-6; N5=T; N6=T; q=2-6; and n=3-10 (preferably n=3-5).

A more preferred TLR21 agonist from the X4 family is where: {N3 [N4]p C G [N5]q N6}=TTCGTT, or TTTCGTTT, for example the oligonucleotides X4-pent and X4-I-minG, respectively, as these provide a good compromise between activity versus size and costs.

Further preferred TLR21 agonists from all the three compound families described, for use in a vaccine according to the invention are represented in Table 1. The EC50 value indicated was determined using the HEK293 cell/pNifTy2 indicator system expressing a chicken TLR21.

The vaccine according to the invention can in principle be of rather simple constitution: the oligodeoxynucleotide, depending on its formulation, can simply be dissolved in a watery buffer, and the avian Herpesvirus vector can be contained in a solution comprising the virus and a buffer that stabilises its viability. When mixed with the pharmaceutically acceptable carrier for the invention, this result in the vaccine according to the invention.

Therefore in a further aspect the invention relates to a method for the preparation of a vaccine according to the invention, comprising the admixing of an avian Herpesvirus vector, an avian TLR21 agonist, both as described for the invention, and a pharmaceutically acceptable carrier.

The resulting product of this method is the vaccine according to the invention, which accelerates the immune response in avians against an antigen expressed by an avian Herpesvirus vector.

The Herpesvirus vector for use in the vaccine according to the invention is prepared using standard procedures of virus culturing. Next to production in host animals, the proliferation in in vitro culture on suitable host cells is preferred, e.g.: in primary cells such as chicken embryo fibroblasts (CEF) (for HVT and MDV), or in an established cell-line such as Leghorn male hepatoma (LMH) cells (for ILTV). Such methods are well known, and are readily applicable by a person skilled in the art. For example: the Herpesvirus vector for the invention is constructed by transfection and recombination and the desired recombinant virus is selected. Next the vector viruses are produced industrially in larger volumes. From such cultures a suspension comprising the virus is harvested, either as infected whole cells or as a cell-sonicate, this suspension is formulated into a vaccine and the virus vector product is packed and stored until further use.

To prepare the vaccine according to the invention, the admixing of oligodeoxynucleotide, vector, and carrier can be done in different ways, and in a different order; for example, two of these three constituents can be pre-mixed with each other, before the third constituent is added. This may be beneficial for a number of economic or practical reasons, e.g. for quality control, cost and labour reduction, or storage and logistic reasons. This way an intermediary product can be prepared and stored, and the final complete vaccine is only prepared shortly before shipment, or even shortly before use.

After extensive testing for quality, quantity and sterility the vaccine can then be released for sale.

General techniques and considerations that apply to the preparation of vaccines are well known in the art and are described for instance in governmental regulations (Pharmacopoeia) and in handbooks such as: "Veterinary vaccinology" and: "Remington" (both supra).

In a preferred embodiment the Herpesvirus vector for the invention is an existing commercial vaccine product, consequently one only has to admix the oligonucleotide as described for the invention, to prepare the vaccine according to the invention. This can be by the producer, under controlled conditions, or simply by a qualified person on the spot of the vaccination. In this last case, the vaccine according to any of the embodiments of the invention can be prepared as a kit of parts, comprising the avian Herpesvirus vector and the oligodeoxynucleotide in separate containers.

Alternatively, the Herpesvirus vector and the oligodeoxynucleotide, both as described for the invention, can be mixed into a composition that is an intermediary product for the vaccine according to the invention, such as a mixture in a stabiliser or diluent. Similar to other conceivable intermediary products this can be advantageous in terms of quality or economy, in preparing a composition in such a way.

Therefore in further aspects, the invention relates to:
- a composition comprising an avian Herpesvirus vector and an oligodeoxynucleotide, both as described for the invention.
- a vaccine for avians comprising a composition according to the invention, and a pharmaceutically acceptable carrier.
- a method for the preparation of a vaccine according to the invention, comprising the admixing of a composition according to the invention, and a pharmaceutically acceptable carrier.
- the use of a composition according to the invention, for the manufacture of a vaccine for avians.

The vaccine according to any of the embodiments of the invention may comprise a stabiliser, e.g. to protect sensitive components from being degraded, to enhance the shelf-life of the vaccine, and/or to improve storage efficiency such as for freezing, or freeze-drying. Generally stabilisers are large molecules of high molecular weight, such as lipids, carbohydrates, or proteins; for instance milk-powder, gelatine, serum albumin, sorbitol, trehalose, spermidine, Dextrane or polyvinyl pyrrolidone, and buffers, such as alkali metal phosphates.

Preferably the stabiliser is free of compounds of animal origin, or even: chemically defined, as disclosed in WO 2006/094.974.

Also preservatives may be added, for example: thimerosal, merthiolate, phenolic compounds, and/or gentamicin.

It goes without saying that admixing other compounds, such as carriers, diluents, emulsions, and the like to a vaccine according to the invention are also within the scope of the invention. Such additives are described in well-known handbooks such as: "Remington", and "Veterinary Vaccinology" (both supra). However none of the vaccine constituents should interfere with the viability or the establishment of a productive infection by the avian Herpesvirus vector, or with the acceleration of the avian immune response by the avian TLR21 agonist.

This also applies to the formulation of the vaccine according to the invention as a freeze-dried product, which may enable prolonged storage at temperatures above zero° C., e.g. at 4° C. However whether this is advantageous in a specific case, depends on the characteristics of the avian Herpesvirus vector used for the invention, as some Herpesviruses, e.g. MDV1, do not survive freeze-drying well.

The vaccine according to the invention may additionally comprise a so-called "vehicle"; this can provide a support for the constituents of the vaccine, to adhere without being covalently bound to it. Such vehicles are i.a. bio-microcapsules, micro-alginates, liposomes, macrosols, aluminium-hydroxide, phosphate, sulphate or -oxide, silica, Kaolin™, and Bentonite™, all known in the art.

An example is a vehicle in which the antigen is partially embedded in an immune-stimulating complex, the so-called ISCOM™ (see EP 109.942).

In addition, the vaccine according to the invention may comprise one or more suitable surface-active compounds or emulsifiers, e.g. a component from the Span™ or Tween™ family.

The skilled person will appreciate that any and all additives are to be verified and tested for compatibility with the avian Herpesvirus vector and the oligodeoxynucleotide for the invention.

The amount of the avian Herpesvirus vector per avian dose of the vaccine according to the invention, is not as critical as it would be for an inactivated type vaccine. This is because the avian Herpesvirus vector will replicate itself and thus multiplies in the target avian up to a level of viremia that is biologically sustainable. Nevertheless, a minimal dose must be given to achieve an effective 'take' of the vector vaccine. In this respect different ways exist to quantify a live Herpesvirus; convenient is one that counts the actual viable virus particles, such as a plaque assay on a susceptible cell-layer. Amounts of the avian Herpesvirus vector for the invention can then be expressed as a number of plaque forming units (pfu). Which dose constitutes an effective inoculum dose depends on the viability and replicative strength of the particular Herpesvirus that is used as vector for the invention.

A preferred amount of the avian Herpesvirus vector for the invention, in the vaccine according to the invention, is between about 10 and about 1×10^7 pfu of the avian Herpesvirus vector per dose, more preferably between 1×10^2 and 1×10^6, between 1×10^3 and 1×10^5, between 1×10^3 and 1×10^4, and even between 1000 and 5000 pfu/dose, in increasing order of preference.

In case the avian Herpesvirus vector for the invention is a cell-bound virus, such as may apply to HVT or MDV, the vector can be administered in cell-associated form. In that case one avian dose comprises between 100 and 10.000 infected host cells per dose, preferably between 100-5000 infected cells, more preferably between 200-2000 infected host cells per dose.

Apart from the accelerated immune protection that the vaccine according to the invention already provides, it can be advantageous to add one or more further immunoactive component(s). Such a component may be an antigen, a further INO, an immune enhancing substance, a cytokine, and/or a vaccine, to create a combination vaccine. This provides advantages in terms of cost, efficiency and animal welfare. Alternatively, the vaccine according to the invention, may itself be added to a vaccine.

The vaccine according to the invention in principle can be administered to target avians by different routes of application, and at different points in their lifetime, provided the inoculated recombinant avian Herpesvirus vector can establish a protective infection against the heterologous antigen. In principle this is irrespective of the avian target's age, weight, sex, immunological status, etc., although it is evidently favourable to vaccinate healthy targets, and to vaccinate as early as possible to withstand the field infection pressure from e.g. MDV, NDV or IBDV. Therefore it is advantageous to apply the vaccine according to the invention as early as possible, preferably at the day of hatch (day 1), or even in ovo, e.g. at 18 days ED. Suitable equipment for automated injection into the egg at industrial scale is available commercially. This provides the earliest possible protection, while minimising labour cost.

Therefore, in a preferred embodiment, the vaccine according to the invention is administered in ovo.

Different in ovo inoculation routes are known, such as into the yolk sac, the embryo, or the allantoic fluid cavity; these can be optimised as required.

Alternatively, a parenteral inoculation of individual avians can be applied. This is preferably applied intramuscular or subcutaneous. Other beneficial immunisation routes are by alimentary, intestinal, or mucosal route; for example by oral, nasal, oro-nasal, or ocular route. This can be achieved by any method of drop- or spray vaccination. A further example of these routes of administration is the convenience and economy of the mass-application.

Formulations of the vaccine according to the invention suitable for injection, are e.g. a suspension, solution, dispersion, or emulsion.

Depending on the route of application of the vaccine according to the invention, it may be necessary to adapt the vaccine composition. This is well within the capabilities of a skilled person, and generally involves the fine-tuning of the efficacy or the safety of the vaccine. This can be done by adapting the vaccine dose, quantity, frequency, route, by using the vaccine in another form or formulation, or by adapting or adding other constituents of the vaccine (e.g. a stabiliser or an adjuvant).

For example, to be suitable for application in ovo, the vaccine composition is required to be very mild, in order not to reduce the hatchability of the eggs. However, even then some reduction in hatchability may still occur, e.g. resulting from mechanical damage to the embryo by the inoculation itself, an infection, etc.

The inventors have established that an oligodeoxynucleotide as described for the invention, can be applied to chickens in ovo, to at least 10 μg per dose, without inducing a manifest pathological reaction. However such an amount may not be economically feasible. Also, the inventors have observed that a specific TLR21 agonist can have an optimal effective dose, such that a higher or lower amount gave a lower effect of immune-acceleration; e.g. in one animal experiment a dose of the avian TLR21 agonist of 0.1 μg per chick was better than doses of 0.01 μg or 1 μg per chick. The skilled person will realise this may depend on a variety of parameters such as: the specific activity of the oligodeoxynucleotide used, the species of avian target, the formulation, the administration route, etc., and he/she will be able to optimise such conditions by routine experimentation.

The quantification of an oligodeoxynucleotide for use in the invention can conveniently be done in a number of ways, e.g. by column chromatography with detection via UV absorption spectrophotometry at the calculated extinction coefficient of the specific oligodeoxynucleotide to be tested, typically in the range of about 250-280 nm.

Therefore, for the invention the preferred amount of the oligodeoxynucleotide as described for the invention per avian dose is between 0.1 ng and 1 mg, more preferred between 1 ng and 100 μg, even more preferred between about 10 ng and about 10 μg per avian dose, and most preferred between about 30 ng and 3 μg per avian dose.

The vaccine according to the invention can equally be used as prophylactic and as therapeutic treatment, and interferes both with the establishment and/or with the progression of an avian-pathogen, the infection, or its clinical signs of disease.

Also, the vaccine according to the invention can effectively serve as a priming vaccination, which can later be followed and amplified by a booster vaccination, with either a vaccine according to the invention, or with an inactivated vaccine for avians.

The dosing scheme for the administration of the vaccine according to the invention to the target avian can be in single or in multiple doses, which may be given at the same time or sequentially, in a manner compatible with the required dosage and formulation of the vaccine, and in such an amount as will be immunologically effective for the target avian.

The protocol for the administration of the vaccine according to the invention ideally is integrated into existing vaccination schedules of other vaccines for that target avian.

Preferably the vaccine according to the invention is applied only once, either at the day of hatch, or in ovo at day 18 ED. However, depending on the type of avian to be vaccinated, and its breeding schedule, the avian may need to be revaccinated, once, several times, or even periodically.

The volume per avian dose of the vaccine according to the invention can be optimised according to the intended route of application: in ovo inoculation is commonly applied with a volume between about 0.05 and 0.5 ml/egg, and parenteral injection is commonly done with a volume between about 0.1 and 1 ml/avian. The optimisation of the vaccine dose volume is well within the capabilities of the skilled artisan.

The vaccine according to the invention in effect is a 'marker vaccine' for the micro-organism against which the vector's expressed heterologous gene protects, because the immunity it generates is only directed against one (or a few) protein(s) from this micro-organism. This allows the "differentiation of infected and vaccinated animals", the so-called 'DIVA' approach. This can conveniently be performed by a serological assay such as an ELISA or immuno-fluorescence assay.

The advantageous effect of the invention: the acceleration of the immune response in avians against an antigen expressed and delivered by an avian Herpesvirus vector, is achieved upon the administration of the avian Herpesvirus vector and the oligodeoxynucleotide, both as described for the invention, to avians. There are several ways wherein this administration can be done, and the advantageous effect is obtained. These lead to different aspects and embodiments of the invention. In particular: avians can be immunised with a vaccine according to one of the embodiments of the invention, or with the separate constituents of such a vaccine. Details of these various embodiments are described and exemplified herein.

For example the avian Herpesvirus vector and the oligodeoxynucleotide, both as described for the invention, can be combined into one vaccine, either from separate components, or from an intermediary composition as described. Alternatively, avians can be inoculated with the vector and the oligodeoxynucleotide separately, for example when the vector is already formulated as a vaccine, then the oligodeoxynucleotide can be added to that vaccine, or administered separately. When given as separate inoculations, then preferably the inoculation of the avian Herpesvirus vector, and of the oligodeoxynucleotide, both as described for the invention, to a target avian, are no more than 3 days apart. This is exemplified below, where it is described that the separate administration of an oligodeoxynucleotide as described for the invention, up to three days after the administration of an avian Herpesvirus vector, was still effective in accelerating the immune response.

Consequently, for the invention, the avian Herpesvirus vector and the oligodeoxynucleotide, both as described for the invention, can be administered to avians in a single, or a dual administration; the single administration is when both are combined in a single formulation; the dual administration can be by administration at different times, or simultaneous, but then at different sites on the body, by different routes, or by different methods. When administered separately, the vector and the oligodeoxynucleotide are administered to the target avian no more than 3 days apart, whereby either one can be given first.

Therefore in a further aspect the invention relates to a method for the vaccination of avians, comprising the administration to avians of an avian Herpesvirus vector as described for the invention, and of an oligodeoxynucleotide as described for the invention.

The administration can be combined, or separated by site, route, or method. A skilled person is capable of testing variations of these possible ways of administration, to arrive at a protocol that is optimal for a certain avian species, or a desired immune-protection.

In a further aspect, the invention relates to a TLR21 agonist as described for the invention for use in accelerating the immune response in avians, against an antigen expressed by an avian Herpesvirus vector as described for the invention.

In a further aspect the invention relates to a TLR21 agonist as described for the invention, for use in a method of vaccination of avians, to accelerate the immune response in avians against an antigen expressed by an avian Herpesvirus vector as described for the invention.

In a further aspect the invention relates to the use of a TLR21 agonist as described for the invention, for the manufacture of a vaccine for avians, to accelerate the immune response in avians against an antigen expressed by an avian Herpesvirus vector as described for the invention.

In a further aspect the invention relates to a method for accelerating the immune response in avians against an antigen expressed by an avian Herpesvirus vector as described for the invention, comprising the administration to avians of a TLR21 agonist as described for the invention.

The invention will now be further described by the following, non-limiting, examples.

EXAMPLES

Example 1: Synthesis and Purification of TLR21 Agonists

Oligodeoxynucleotides for use in experiments for the present invention, were ordered from BioSpring (Frankfurt a. M., Germany), and were received purified and lyophilised at an indicated amount. These were diluted in a suitable buffer, depending on the experimental use. The concentration was checked occasionally by size exclusion chromatography combined with UV monitoring, but was found to be correct in all cases.

Example 2: Avian Herpesvirus Vector

The avian Herpesvirus vector used for some of the experiments, HVT-F-VP2, was based on HVT, and comprised the F gene from NDV, as well as the VP2 gene from IBDV, both inserted into the Us2 region. Construction of the vector, production on cells, quantification, etc., were all as described in WO 2013/057.235.

Example 3: In Vitro Tests of Avian TLR21 Agonist Activity

The use of the HEK293 cell-line transformed with a chicken TLR21 receptor, for the testing and qualification of avian TLR21 agonist candidates has been described e.g. in WO 2012/089.800. However in brief: HEK293 cells were transfected with an NFkappaB activation reporter plasmid: pNiFty2-SEAP (InvivoGen, San Diego, Calif., USA). Clonal cell lines were selected, and used for the transfection with a chicken TLR21 gene. Again clonal cell lines were selected. These were used for the detection of NFkappaB activation upon incubation with different concentrations of avian TLR21 agonistic oligodeoxynucleotides. Read out was by colorimetric detection of the secreted SEAP (secreted embryonic alkaline phosphatase) activity, by OD 405 nm spectrophotometry. This was plotted as mOD405 nm/min, as function of a gradient of the agonist's concentration. The relevant results were those with a high rate of colour formation, at a relatively low agonist concentration.

Example 4: In Vivo Test of Avian TLR21 Agonist Activity on Avian Herpesvirus Vector Induced Immunity 4.1. Introduction This experiment was designed to test the in vivo effect of a TLR21 agonist: X4-1-minG (EC50=1.9 nM) on avian Herpesviral vector induced immunity in chickens. Different time-points for the administration of the TLR21 agonist to vector vaccinated birds were tested, for one amount of the agonist.

4.2. Materials and Methods 4.2.1. Experimental Design

Seven (7) groups of 1 day-old SPF White Leghorn chicks (n=25/group) were vaccinated once s.c. at the base of the neck with HVT-F-VP2 vector (expressing the NDV-F and the IBDV-VP2 antigens): groups 3-9. Group 2 was only s.c. injected with TLR21 agonist at T=0, and group 1 was the unvaccinated challenge control.

At several time points post vaccination a TLR21 agonist was s.c. injected at the base of the neck according to the treatment schedule for grouping and dosing. Blood samples were taken before vaccination (T=0) from 20 hatchmates via bleeding, and at T=2 weeks post-vaccination from 5 randomly picked vaccinated/injected birds from groups 2-9 after which these 40 animals were taken out of the experiment, and formed a new n=20/group. Sera were used to determine the anti-NDV and anti-IBDV antibody titres.

After bloodsampling the 25 non-vaccinated control animals (group 1) were divided at random over the 8 vaccinated/injected groups, i.e. 3 control animals were placed into each group (n=23/group; 1 group with n=24). Subsequently all animals were challenged via the intramuscular (i.m.) route with 0.2 ml (6.0 log 10 EID50) of the NDV Herts 33/56 strain.

4.2.2. Biosafety

Chickens were kept in isolators, under negative pressure, and with Hepa filtered air in/out, to contain the genetically modified vectors and the virulent challenge virus.

4.2.3. Test Materials avian TLR21 agonist: X4-1-minG
Vector vaccine: HVT-F-VP2, passage 6.
Challenge material: Live NDV Herts 33/56, at a titre of: 9.6 log 10 EID50 per ml.
Dosing: 1 dose equals 0.2 ml. The TLR21 agonist was injected at 0.1 µg per dose.

4.2.4. Test Animals

White Leghorn Chicken, specific pathogen free, of mixed sex, 1 day old at the start of the experiment. Chicks were numbered individually by wing-tag. The 25 control chickens of group 1, were numbered with a different coloured tag.

4.2.5. Food and Water

Food and water was available to the animals ad libitum.

4.2.6. Grouping and Dosing

| Group | No. | Vector vaccine (0.2 ml s.c. at T = 0) | s.c. injection of 0.1 ml X4-l-minG (0.1 µg/dose) at different time points post vaccination (p.v.) |
|---|---|---|---|
| 1 | 25 | none | none |
| 2 | 25 | none | T = 0 |
| 3 | 25 | HVT-F-VP2 | none |
| 4 | 25 | HVT-F-VP2 | T = 0 (incorporated into the vaccine) |
| 5 | 25 | HVT-F-VP2 | T = 1 day p.v. |
| 6 | 25 | HVT-F-VP2 | T = 3 days p.v. |
| 7 | 25 | HVT-F-VP2 | T = 6 days p.v. |
| 8 | 25 | HVT-F-VP2 | T = 8 days p.v. |
| 9 | 25 | HVT-F-VP2 | T = 10 days p.v. |

20 hatchmates were bled at T = 0

4.2.7. Vaccination

The animals from the groups 3-9, were vaccinated s.c. with 0.2 ml vector vaccine at the base of neck at the age of 1 day old. Group 2 was injected with only 0.1 ml TLR21 agonist at T=0.

At several time points post vaccination 0.1 ml TLR21 agonist was s.c. injected at the base of the neck in the animals of groups 5-9 according to the "Grouping and dosing" Table. The 25 control animals from group 1, which had a differently coloured number tag, were not vaccinated.

4.2.8. Challenge

At 2 weeks post vaccination all remaining animals in each group were challenge-infected via the injection of 0.2 ml Live NDV Herts 33/56 (6.0 log 10 EID50 per chicken) via the i.m. route in the right leg muscle.

4.2.9. Blood Sampling

Blood samples for serology were taken before vaccination (T=0) from 20 hatchmates via bleeding, and at T=2 weeks post-vaccination from 5 randomly picked vaccinated/injected birds from all vaccinated/injected groups. After bloodsampling, these 40 animals (8 groups of 5 animals) were taken out of the experiment. All blood samples were transported to a laboratory for processing and analysis.

After bloodsampling, but before challenge, the 25 non-vaccinated control animals were divided at random over the 8 vaccinated/injected groups, i.e. 3 control animals were placed in each group (n=23/group, leaving one group with n=24) to serve as sentinels.

4.2.10. Observation for Clinical Signs

Pre-Challenge:

Chickens were observed daily for the presence of clinical signs of disease or other abnormalities, by a qualified person. Chickens showing pain or discomfort, which was considered to be non-transient in nature or likely to become more severe, were sacrificed for animal welfare reasons. Chickens that died or were sacrificed pre-challenge were not submitted for post mortem examination, as no high or unexpected mortalities occurred.

Post-Challenge

For 14 days post-challenge all chickens in all groups were scored daily for the occurrence of clinical evidence of NDV infection or mortality. Data were recorded per animal on special forms. The following score system was used:

0. No occurrence of clinical evidence of Newcastle disease.
1. Occurrence of clinical evidence of Newcastle disease, with central nervous signs like: Clonic spasm, muscular tremors, torticollis, opisthotonos, or paralysis of legs or wings.
2. Mortality caused by NDV challenge. In case animals were sacrificed for animal welfare reasons this was indicated on the form.

4.3. Results

| Gr. | No. | Vector vaccine (0.2 ml s.c. at T = 0) | s.c. injection of 0.1 ml X4-l-minG (0.1 µg/dose) at different time points post vaccination (p.v.) | % survival at 2 w. p.v. |
|---|---|---|---|---|
| 1 | 20 | — | none | None |
| 2 | 20 | — | T = 0 | None |
| 3 | 20 | HVT-F-VP2 | none | 20 |
| 4 | 20 | HVT-F-VP2 | T = 0 (incorporated into the vaccine) | 35 |
| 5 | 20 | HVT-F-VP2 | T = 1 day p.v. | 20 |
| 6 | 20 | HVT-F-VP2 | T = 3 days p.v. | 45 |
| 7 | 20 | HVT-F-VP2 | T = 6 days p.v. | 30 |
| 8 | 20 | HVT-F-VP2 | T = 8 days p.v. | 25 |
| 9 | 20 | HVT-F-VP2 | T = 10 days p.v. | 10 |

4.4. Conclusions

The administration of an avian TLR21 agonist, simultaneous with, or shortly after the administration of an avian Herpesvirus vector provided for a significant acceleration of the immune response against the heterologous antigen that was expressed and delivered by the vector. This is demonstrated by the percentage of survivors of a severe NDV challenge infection, that was given quite early—namely at two weeks—after the vector vaccination.

While none of the chickens survived that were unvaccinated (group 1) or received only agonist (group 2), and only 20% of the vector vaccinates (group 3) survived, the survival of vaccinates receiving both vector and agonist was mostly higher, giving 30, 35 and even 45% challenge survivors (groups 4, 6, and 7). The 20% survival in the group receiving the agonist at 2 days p.v. (group 5) is probably the result of a variability in the trial. After 8 days p.v. the agonist could no longer accelerate the immune response to the vector-expressed heterologous antigen (group 9).

Consequently, the agonist alone could not induce an immune protection. Also, at this early time after vaccination, the vector vaccine alone had only established a modest immunity against the NDV-F antigen. However, with the combined administration of vector and agonist, an early onset of immunity could be achieved, resulting in a challenge survival rate that more doubled.

Example 5: Further In Vivo Test of Avian TLR21 Agonist Activity on Avian Herpesvirus Vector Induced Immunity A further animal trial in chickens was performed, in essentially the same way as described in Example 4, but with some modifications: the main difference being that all vaccinations comprised both the avian Herpesvirus vector and the oligodeoxynucleotide in the same inoculation, and these were thus administered at the same time (day 0).

Other variations from the protocol of Example 4 were that another avian TLR21 agonist was used: X4-pent (SEQ ID NO: 4) (EC50=430 pM), and that this agonist was tested in three different amounts/dose.

5.1. Results

| Gr. | No. | Vector vaccine | Amount of X4-pent | % survival at 2 w. p.v. |
|---|---|---|---|---|
| 1 | 20 | none | none | None |
| 2 | 20 | HVT-F-VP2 | none | 10 |
| 3 | 20 | HVT-F-VP2 | 0.1 µg | 45 |
| 4 | 20 | HVT-F-VP2 | 1.0 µg | 20 |
| 5 | 20 | HVT-F-VP2 | 20 µg | 20 |

5.2. Conclusions

Again, the addition of an avian TLR21 agonist demonstrated significant acceleration of the immune response against the heterologous antigen expressed and delivered by the avian Herpesvirus vector: at two weeks post vaccination, up to 45% of vaccinates that received both the vector vaccine and the agonist (group 3) were protected against a severe NDV challenge infection. Whereas none of the unvaccinated chickens were protected (group 1), and only 10% of the vaccinates receiving only the vector vaccine (group 2).

Notably: the higher amounts of the agonist per dose (1 or 20 µg—groups 4 and 5) did not improve the immune acceleration, as both provided less immune acceleration than the lowest amount of 0.1 µg per animal dose (group 3).

The invention claimed is:

1. A vaccine comprising a live Herpesvirus of turkeys (HVT) vector, an oligodeoxynucleotide, and a pharmaceutically acceptable carrier, wherein the live HVT vector comprises a heterologous nucleotide sequence encoding an antigen from a micro-organism that is pathogenic to avians; and wherein the oligodeoxynucleotide is an avian Toll-like receptor (TLR) 21 agonist.

2. A method of administering a vaccine against a micro-organism that is pathogenic to an avian comprising administering the vaccine of claim 1 to the avian.

3. The vaccine of claim 1, wherein the avian TLR21 agonist comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17.

4. A method for preparing the vaccine of claim 3, comprising the admixing the live HVT vector, the TLR21 agonist, and a pharmaceutically acceptable carrier.

5. A composition comprising the live HVT vector and the TLR21 agonist of claim 3.

6. A vaccine for avians comprising the composition of claim 5, and a pharmaceutically acceptable carrier.

7. A method for preparing a vaccine comprising admixing the composition of claim 5 and a pharmaceutically acceptable carrier.

8. A method of administering a vaccine against a micro-organism that is pathogenic to an avian comprising administering the vaccine of claim 3 to the avian.

9. The vaccine of claim 3, wherein the avian TLR21 agonist comprises the nucleotide sequence of SEQ ID NO: 1.

10. A composition comprising the live HVT vector and the TLR21 agonist of claim 9.

11. A vaccine for avians comprising the composition of claim 10 and a pharmaceutically acceptable carrier.

12. A method of administering a vaccine against a micro-organism that is pathogenic to an avian comprising administering the vaccine of claim 9 to the avian.

13. The vaccine of claim 3, wherein the avian TLR21 agonist comprises the nucleotide sequence of SEQ ID NO: 4.

14. A composition comprising the live HVT vector and the TLR21 agonist of claim 13.

15. A vaccine for avians comprising the composition of claim 14 and a pharmaceutically acceptable carrier.

16. A method of administering a vaccine against a micro-organism that is pathogenic to an avian comprising administering the vaccine of claim 13 to the avian.

* * * * *